United States Patent [19]

Beasley et al.

[11] Patent Number: 5,753,666
[45] Date of Patent: May 19, 1998

[54] QUINOLONES AND THEIR THERAPEUTIC USE

[75] Inventors: Steven Colin Beasley; John Gary Montana; Hazel Joan Dyke; Alan Findlay Haughan; George Martin Buckley; Andrew Douglas Baxter, all of Cambridge, United Kingdom

[73] Assignee: Chiroscience Limited, Cambridge, United Kingdom

[21] Appl. No.: 691,339

[22] Filed: Aug. 2, 1996

[30] Foreign Application Priority Data

| Aug. 2, 1995 | [GB] | United Kingdom | 9515812 |
| Nov. 20, 1995 | [GB] | United Kingdom | 9523679 |
| Mar. 20, 1996 | [GB] | United Kingdom | 9605865 |
| Jun. 7, 1996 | [GB] | United Kingdom | 9611898 |

[51] Int. Cl.$^6$ .................... A01N 43/54; C07D 471/00
[52] U.S. Cl. ................................ 514/258; 544/279
[58] Field of Search ........................... 544/279; 514/258

[56] References Cited

U.S. PATENT DOCUMENTS 4,621,088  11/1986  Larmelle et al. ................ 514/300

OTHER PUBLICATIONS

Goodman & Gilman, "The Pharmacological Basis of Therapeutics", 9th ed., 1990, pp. 286–289, 618–620, 654, 655, 659–661, 832–836, 1291–1294, 1306.

*Primary Examiner*—Mukund J. Shah
*Assistant Examiner*—Tamthom T. Ngo
*Attorney, Agent, or Firm*—Saliwanchik, Lloyd & Saliwanchik

[57] ABSTRACT

1-Alkyl-substituted-quinolone-3-carboxamides have therapeutic utility via inhibition of Phosphodiesterase IV esterase and/or Tumor Necrosis Factor activity.

31 Claims, No Drawings

QUINOLONES AND THEIR THERAPEUTIC USE

FIELD OF THE INVENTION

The present invention relates to the therapeutic use of quinolone derivatives, and to certain novel such compounds.

BACKGROUND OF THE INVENTION

Quinolone compounds are known primarily as antibacterial agents (see JP-A-05025162; U.S. Pat. No. 5,037,834; EP-A-0420069; WO-A-9410163; JP-A-02040379; EP-A-0343560; DE-A-3816119; EP-A-0304158; and DE-A-3641312) or antiviral agents (U.S. Pat. No. 4,959,363) but also as inhibitors of 5-lipoxygenase (JP-A-02124871), cardiotonics and vasodilators (JP-A-01061461) and 5-$HT_3$ antagonists for the treatment of peripheral disorders associated with pain (WO-A-9501793 and GB-A-2236751). None of these publications discloses utility as PDE IV inhibitors.

Phosphodiesterases regulate cyclic AMP/GMP concentrations. Phosphodiesterase IV (PDE IV) has been demonstrated to be a principal regulator of cyclic AMP in respiratory smooth muscle and inflammatory cells [see Torphy and Cieslinski, Molecular Pharmacology 37:206 (1990); Dent et al, British Journal of Pharmacology, 90:163p (1990)]. Inhibitors of phosphodiesterase IV have been implicated as being bronchodilators and asthma-prophylactic agents, as agents for inhibiting eosinophil accumulation and the function of eosinophils [see for example Gembycz and Dent, Clinical and Experimental Allergy 22:337 (1992)] and for treating other diseases and conditions characterised by, or having an etiology including, morbid eosinophil accumulation. Inhibitors of PDE IV are also implicated in treating inflammatory diseases, proliferative skin disease and conditions associated with cerebral metabolic inhibition.

Tumour Necrosis Factor (TNF) is a serum glycoprotein. Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft vs. host reaction, allograft rejections, fever and myalgias due to infection, such as influenza, cachexia secondary to infection or malignancy, cachexia secondary to human acquired immune deficiency syndrome (AIDS), AIDS, ARC (AIDS-related complex), keloid formation, scar tissue formation, Crohn's disease, ulcerative colitis, or pyresis, in addition to a number of autoimmune diseases, such as multiple sclerosis, autoimmune diabetes and systemic lupus erythematosis.

AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell mediated immunity is impaired and infected individuals manifest severe opportunistic infections and/or unusual neoplasms. HIV entry into the T lymphocyte requires T lymphocyte activation. Viruses such as HIV-1 or HIV-2 infect T lymphocytes after T cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication.

Cytokines, specifically TNF, are implicated in activated T-cell mediated HIV protein expression and/or virus replication by playing a role in maintaining T lymphocyte activation. Therefore, interference with cytokine activity such as by inhibition of cytokine production, notably TNF, in an HIV-infected individual aids in limiting the maintenance of T cell activation, thereby reducing the progression of HIV infectivity to previously uninfected cells which results in a slowing or elimination of the progression of immune dysfunction caused by HIV infection. Monocytes, macrophages, and related cells, such as Kupffer and glial cells, have also been implicated in maintenance of the HIV infection. These cells, like T cells, are targets for viral replication and the level of viral replication is dependent upon the activation state of the cells [see Rosenberg et al, The Immunopathogenesis of HIV Infection, Advances in Immunology, Vol. 57, (1989)]. Monokines, such as TNF, have been shown to activate HIV replication in monocytes and/or macrophages [See Poli et al, Proc. Natl. Acad. Sci., 87:782–784 (1990)]. Therefore, inhibition of monokine production or activity aids in limiting HIV progression as stated above for T cells.

TNF has also been implicated in various roles with other viral infections, such as the cytomegalovirus (CMV), influenza virus, adenovirus, and the herpes virus for similar reasons as those noted.

TNF is also associated with yeast and fungal infections. Specifically, *Candida albicans* has been shown to induce TNF production in vitro in human monocytes and natural killer cells. [See Riipi et al, Infection and Immunity, 58(9) :2750–54 (1990); and Jafari et al, Journal of Infectious Diseases, 164:389–95 (1991). See also Wasan et al, Antimicrobial Agents and Chemotherapy, 35(10):2046–48, (1991); and Luke et al, Journal of Infectious Diseases, 162:211–214, (1990)].

The ability to control the adverse effects of TNF is furthered by the use of the compounds which inhibit TNF in mammals who are in need of such use. There remains a need for compounds which are useful in treating TNF-mediated disease states which are exacerbated or caused by the excessive and/or unregulated production of TNF.

U.S. Pat. No. 4,786,644 discloses a variety of compounds including what may be quinolone-3-carboxamides. There is also an aryl substituent at the 1-position.

U.S. Pat. No. 4,621,088 discloses 1-ethylquinolone-3-carboxamides, and heterocyclic analogues, having an acyl substituent on the carboxamide group; the acyl substituent may be cyclohexylmethyl carrying a COOH group. These compounds are disclosed as having an antiallergic action.

U.S. Pat. No. 3,524,858 and GB-A-1191443 disclose, inter alia, 1-alkylquinolone-3-carboxamides having an aryl or aralkyl substituent on the carboxamide group. These compounds are disclosed as having anti-viral activity.

Other quinolone-3-carboxamides are known, in which there is an optionally-substituted phenyl substituent on the carboxamide group. None of these disclosures mentions utility as PDE IV inhibitors.

SUMMARY OF THE INVENTION

This invention relates to compounds, many of which are novel, which can be used to treat disease states, for example disease states associated with proteins that mediate cellular activity, for example by inhibiting tumour necrosis factor and/or by inhibiting phosphodiesterase IV. According to the invention, these compounds are of formula (I):

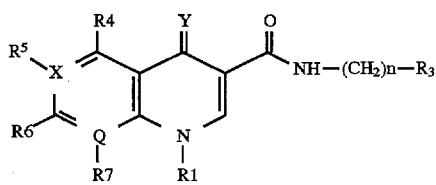

in which:
- $R^1$ is $C_{1-6}$ alkyl, $C_{1-6}$ alkylcycloalkyl, $C_{1-6}$ alkylheterocyclo, $C_{1-6}$ alkylaryl or $C_{1-6}$ alkylheteroaryl, any of which is optionally substituted by one or more substituents chosen from halo, $C_{1-6}$ alkoxy, hydroxy, CN, $CO_2H$ (or $C_{1-6}$ alkyl esters or $C_{1-6}$ alkyl amides thereof), $C_{1-6}$ alkyl, $NR^9R^{10}$ and $SO_2NR^{11}R^{12}$;
- $R^3$ is phenyl, pyridyl, thienyl, furyl, pyrazinyl, pyridazinyl, pyrimidinyl or $C_{3-20}$ cycloalkyl, to any of which is optionally fused a second, carbocyclic or heterocyclic ring, and wherein the or each ring is optionally substituted at any available position by one or more substituents selected from halogen, $C_{1-6}$ alkoxy, OH, CN, COOH (or $C_{1-6}$ alkyl esters or $C_{1-6}$ alkyl amides thereof), $C_{1-6}$ alkyl, $C_{1-6}$ haloalkyl, $NR^9R^{10}$, $SO_2NR^{11}R^{12}$, aryl, heteroaryl, cycloalkyl and heterocyclo;
- Y is O or S;
- X is C or N (in which case $R^5$ is absent);
- Q is C or N (in which case $R^7$ is absent), provided that at least one of X and Q is N;
- $R^4$, $R^5$, $R^6$ and $R^7$ are the same or different and are each H, halo, $C_{1-6}$ alkoxy, hydroxy, CN, $CO_2H$ (or $C_{1-6}$ alkyl esters thereof or $C_{1-6}$ alkyl amides thereof), $NR^9R^{10}$ or $C_{1-6}$ alkyl, in which alkyl may be optionally substituted by halo, $C_{1-6}$ alkoxy, hydroxy, CN, $CO_2H$ (or $C_{1-6}$ alkyl esters thereof or $C_{1-6}$ alkyl amides thereof), $NR^9R^{10}$ or $SO_2NR^{11}R^{12}$, or any two adjacent groups $R^4$-$R^7$ and the C atoms to which they are attached form a 5 or 6-membered ring containing 0, 1 or 2 heteroatoms;
- either $R^9$ and $R^{10}$ are the same or different and are each H, $C_{1-6}$ alkyl, aryl, heteroaryl, $COCF_3$, $SO_2CF_3$, cycloalkyl, $C_{1-6}$ alkylcarbonyl, arylcarbonyl, $C_{1-6}$ alkoxycarbonyl, arylsulphonyl or $C_{1-6}$ alkylsulphonyl; or $NR^9R^{10}$ is a 5 or 6-membered ring such as a pyrrolidine, piperidine, morpholine or piperazine ring;
- $R^{11}$ and $R^{12}$ are the same or different and are each H, $C_{1-6}$ alkyl or cycloalkyl; and
- n=0–3;
- or a pharmaceutically-acceptable salt, solvate, hydrate or combination thereof.

Compounds of U.S. Pat. No. 4,621,088 are excluded. Known N-arylquinolone-3-carboxamides are excluded, but are claimed for their first therapeutic use.

DESCRIPTION OF THE INVENTION

Certain compounds of formula I are preferred; see claims 2 etc.

Suitable pharmaceutically acceptable salts are pharmaceutically acceptable base salts and pharmaceutically acceptable acid addition salts. Certain of the compounds of formula (I) which contain an acidic group form base salts. Suitable pharmaceutically acceptable base salts include metal salts, such as alkali metal salts for example sodium salts, or organic amine salts such as that provided with ethylenediamine.

Certain of the compounds of formula (I) which contain an amino group form acid addition salts. Suitable acid addition salts include pharmaceutically acceptable inorganic salts such as the sulphate, nitrate, phosphate, borate, hydrochloride and hydrobromide and pharmaceutically acceptable organic acid addition salts such as acetate, tartrate, maleate, citrate, succinate, benzoate, ascorbate, methane-sulphate, α-ketoglutarate, α-glycerophosphate and glucose-1-phosphate. The pharmaceutically acceptable salts of the compounds of formula (I) are prepared using conventional procedures.

It will be appreciated by those skilled in the art that some compounds of formula (I) can exist in more than one tautomeric form. This invention extends to all tautomeric forms.

It will be appreciated that some of the compounds according to the invention can contain one or more asymmetrically substituted carbon and/or sulphur atoms. The presence of one or more of these asymmetric centers in a compound of formula (I) can give rise to stereoisomers, and in each case the invention is to be understood to extend to all such stereoisomers, including enantiomers, and diastereoisomers and mixtures including racemic mixtures thereof.

When used herein the term alkyl whether used alone or when used as part of another group includes straight and branched chain alkyl groups of about 1 to about 6 carbon atoms. Halo or halogen means fluoro, chloro, bromo or iodo. The term haloallyl means an alkyl group as previously defined substituted by one or more halo atoms where halo is as previously defined. Cycloallyl includes a non-aromatic cyclic or multicyclic ring system of about 3 to 10 carbon atoms. The cyclic alkyl may optionally be partially unsaturated. Alkylcycloalkyl means an alkyl-cycloalkyl group where alkyl and cycloalkyl are as previously defined. Alkoxy means an alkyl-O-group in which the alkyl group is as previously described. Alkyl amide includes both monoalkyl and dialkyl amides, in which the alkyl groups (previously defined) may be the same or different. Alkylcarbonyl means an alkyl-CO— group in which the alkyl group is as previously described. Aryl indicates carbocyclic radicals containing about 6 to 10 carbon atoms. Alkylaryl means an alkyl-aryl group wherein the aryl and alkyl are as described herein. Heteroaryl means about a 5 to about a 10 membered aromatic monocyclic or multicyclic ring system in which one or more of the atoms in the ring system is an element other than carbon, chosen from nitrogen, oxygen and sulphur. Heterocyclo means an about 5 to about 10 membered saturated or partially saturated monocyclic or multicyclic ring system in which one or more of the atoms in the ring system is an element other than carbon, chosen from nitrogen, oxygen and sulphur. Carbocylic means a monocyclic or multicyclic ring system of about 5 to about 10 carbon atoms; such a ring may be saturated, partially saturated or aromatic in nature. Alkylheteroaryl means an alkyl-heteroaryl group wherein the alkyl and heteroaryl are as described herein. Alkylheterocyclo means an alkyl-heterocyclo group wherein the alkyl and heterocyclo are as described herein. Arylcarbonyl means an aryl-CO— group. Arylsulphonyl means an aryl-$SO_2$— group. Alkylsulphonyl means an alkyl-$SO_2$— group. Alkoxycarbonyl means an alkoxy-CO group.

In all cases, $R^1$ includes an alkyl chain. It is optionally substituted by cycloalkyl, heterocyclo, aryl or heteroaryl. The whole group $R^1$ may then also optionally be substituted as defined above, by halo etc.

"TNF mediated disease or disease states" means any and all disease states in which TNF plays a role, either by production of TNF itself, or by TNF causing another cytokine to be released, such as but not limited to IL-1 or IL-6. A disease state in which IL-1, for instance, is a major component, and whose production or action is exacerbated or secreted in response to TNF, would therefore be considered a disease state mediated by TNF. As TNF-β (also known as lymphotoxin) has close structural homology with TNF-α (also known as cachectin), and since each induces similar biologic responses and binds to the same cellular receptor, both TNF-α and TNF-β are inhibited by the compounds of the present invention and thus are herein referred to collectively as "TNF" unless specifically mentioned otherwise.

This invention relates to a method for mediating or inhibiting the enzymatic activity or catalytic activity of PDE IV in a mammal in need thereof and for inhibiting the production of TNF in a mammal in need thereof, which comprises administering to said mammal an effective amount of a compound of Formula (I) or a pharmaceutically acceptable salt thereof.

PDE IV inhibitors are useful in the treatment of a variety of allergic and inflammatory diseases, including: asthma, chronic bronchitis, atopic dermatitis, atopic eczema, allergic rhinitis, allergic conjunctivitis, vernal conjunctivitis, inflammation of the eye, allergic responses in the eye, eosinophilic granuloma, psoriasis, Bechet's disease, erythematosis, anaphylactoid purpura nephritis, joint inflammation, arthritis, rheumatoid arthritis and other arthritic conditions such as rheumatoid spondylitis and osteoarthritis, septic shock, ulcerative colitis, Crohn's disease, reperfusion injury of the myocardium and brain, chronic glomerulonephritis, endotoxic shock and adult respiratory distress syndrome. In addition, PDE IV inhibitors are useful in the treatment of diabetes insipidus and conditions associated with cerebral metabolic inhibition, such as cerebral senility, senile dementia (Alzheimer's disease), memory impairment associated with Parkinson's disease, depression and multi-infarct dementia. PDE IV inhibitors are also useful in conditions ameliorated by neuroprotectant activity, such as cardiac arrest, stroke and intermittent claudication. Additionally, PDE IV inhibitors could have utility as gastroprotectants. A special embodiment of the therapeutic methods of the present invention is the treatment of asthma.

The viruses contemplated for treatment herein are those that produce TNF as a result of infection, or those which are sensitive to inhibition, such as by decreased replication, directly or indirectly, by the TNF inhibitors of Formula (I). Such viruses include, but are not limited to HIV-1, HIV-2 and HIV-3, cytomegalovirus (CMV), influenza, adenovirus and the Herpes group of viruses, such as, but not limited to, Herpes zoster and Herpes simplex.

This invention more specifically relates to a method of treating a mammal, afflicted with a human immunodeficiency virus (MIV), which comprises administering to such mammal an effective TNF inhibiting amount of a compound of Formula (I) or a pharmaceutically acceptable salt thereof.

The compounds of this invention may also be used in association with the veterinary treatment of animals, other than humans, in need of inhibition of TNF production. TNF mediated diseases for treatment, therapeutically or prophylactically, in animals include disease states such as those noted above, but in particular viral infections. Examples of such viruses include, but are not limited to feline immunodeficiency virus (FIV) or other retroviral infection such as equine infectious anaemia virus, caprine arthritis virus, visna virus, maedi virus and other lentiviruses.

The compounds of this invention are also useful in treating parasite, yeast and fungal infections, where such yeast and fungi are sensitive to upregulation by TNF or will elicit TNF production in vivo. A preferred disease state for treatment is fungal meningitis.

The compounds of formula (I) are preferably in pharmaceutically acceptable form. By pharmaceutically acceptable form is meant, inter alia, of a pharmaceutically acceptable level of purity excluding normal pharmaceutical additives such as diluents and carriers, and including no material considered toxic at normal dosage levels. A pharmaceutically acceptable level of purity will generally be at least 50% excluding normal pharmaceutical additives, preferably 75%, more preferably 90% and still more preferably 95%.

Compounds of the general formula (I) may be prepared by any suitable method known in the art and/or by the following processes, which itself forms part of the invention.

Thus, for example, compounds according to the invention may be prepared by the following process. In the description and formulae below the groups $R^1$, etc. are as defined above, except where otherwise indicated. It will be appreciated that functional groups, such as amino, hydroxyl or carboxyl groups, present in the various compounds described below, and which it is desired to retain, may need to be in protected form before any reaction is initiated. In such instances, removal of the protecting group may be the final step in a particular reaction. Suitable protecting groups for such functionality will be apparent to those skilled in the art. For specific details see "Protective Groups in Organic Synthesis", Wiley Interscience, T W Greene, PGM Wuts. Thus the process for preparing compounds of formula (I) in which contain $R^4$ is $CO_2H$ comprises deprotecting (for example by hydrolysis) a compound of formula (I) in which $R^4$ is $CO_2R$ wherein R represents a suitable protecting group (eg methyl).

A process for preparing a compound of formula (I) comprises coupling an acid of formula (III)

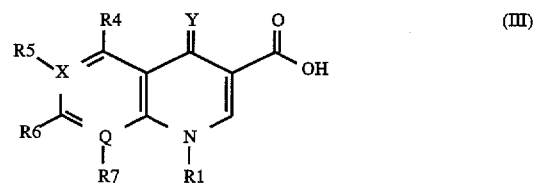

or an activated derivative thereof, with an amine of formula (IV)

$R_3(CH_2)_nNH_2$  (IV)

Amines of formula (IV) may be commercially available or can be readily obtained from commercially available starting materials using methods known to those skilled in the art. Some of the amines of formula (IV) are conveniently prepared by reductive amination of an appropriate carbonyl compound with a suitable amine. This amination may be carried out under any suitable standard conditions known to those skilled in the art.

Active derivatives of acids of formula (III) include for example acid anhydrides or acid halides, such as acid chlorides.

The coupling reaction may be performed using standard conditions for amination reactions of this type. Thus, the reaction may be achieved in a solvent, for example an inert organic solvent such as an ether, eg. a cyclic ether such as tetrahydrofuran, an amide, eg. a substituted amide such as dimethylformamide, or a halogenated hydrocarbon such as dichloromethane at a low temperature eg. –30° C. to ambient temperature, such as –20° C. to 0° C., optionally in the presence of a base, eg. an organic base such as an amine, eg. triethylamine or a cyclic amine such as N-methylmorpholine. Where an acid of formula (III) is used, the reaction may additionally be performed in the presence of a condensing agent, for example a diimide such as N,N'-dicyclohexylcarbodiimide, advantageously in the presence of a triazole such as 1-hydroxybenzotriazole. Alternatively, the acid may be reacted with a chloroformate, for example ethyl chloroformate, prior to reaction with the amine of formula (IV).

Acids of general formula (III) are either commercially available or may be prepared using methods well known to those skilled in the art, e.g. the procedure of Kaminsky and Meltzer, *J. Med. Chem.* (1968) 11: 160–164. This procedure includes hydrolysis of the corresponding ester of general formula (V)

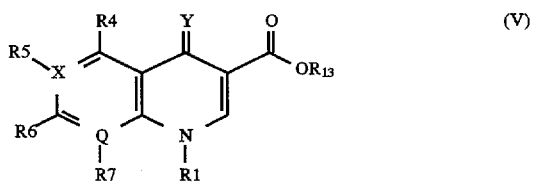

where $R^{13}$ represents an alkyl group such as methyl, ethyl, benzyl or tert-butyl.

Compounds of formula (V) where Y is S may be derived from the corresponding compounds where Y is O using standard conditions for sulphurisation of such compounds. For example, suitable conditions comprise reaction with phosphorus pentasulphide ($P_4S_{10}$) in an organic solvent such as pyridine at from ambient temperature to the reflux temperature of the solvent. The reflux temperature is preferred.

Esters of general formula (V) where Y is O may be prepared by the alkylation of a compound of formula (VI)

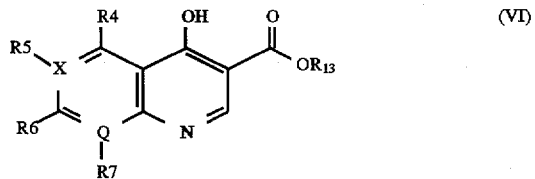

with an alkylating agent of general formula (VII)

as described by Kamisky and Meltzer, supra, wherein G represents a suitable leaving group (eg. a halide such as bromide or an alkylsulphonate ester such as trifluoromethanesulphonate).

Compounds of general formula (VI) may be generated by cyclisation of an ester of formula (VIII)

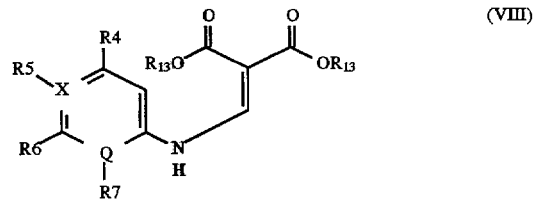

under suitable standard conditions known to those skilled in the art, for example those described by Kaminsky and Meltzer, supra. Suitable conditions include, for example, heating to reflux in a eutectic mixture of diphenyl ether and biphenyl.

Compounds of formula (VIII) may be prepared by the reaction of an aniline of general formula (IX)

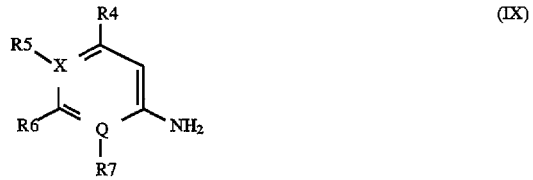

with a dialkyl alkoxyethylidinemalonate of general formula (X)

wherein $R^{13}$ is previously defined and $R^{14}$ is a lower alkyl group such as methyl or ethyl. The reaction between (IX) and (X) may be carried out under suitable standard conditions known to those skilled in the art, for example those described by Kaminsky and Meltzer, supra. For example, the reaction may be carried out at elevated temperature, for example 80°–150° C., in an inert solvent (such as xylene) or in the absence of solvent, preferably in the absence of solvent.

Many compounds of formulae (VII), (IX) and (X) are commercially available or can be readily obtained from commercially available starting materials using methods known to those skilled in the art.

Compounds of formula (I) may also be prepared by interconversion of other compounds of formula (I). Thus, for example, a compound of formula (I) wherein $R^4$ is a $C_{1-6}$ alkoxy group may be prepared by appropriate alkylation of a compound of formula (I) wherein $R^4$ is a hydroxy group.

Any mixtures of final products or intermediates obtained can be separated on the basis of the physico-chemical differences of the constituents, in known manner, into the pure final products or intermediates, for example by chromatography, distillation, fractional crystallization, or by formation of a salt if appropriate or possible under the circumstances. It will be appreciated that where a particular stereoisomer of formula (I) is required, this may be obtained by conventional resolution techniques such as high performance liquid chromatography. Where desired, however, appropriate homochiral starting materials may be used in the reaction sequence to yield a particular stereoisomer of formula (I).

A compound of formula (I) or where appropriate a pharmaceutically acceptable salt thereof and/or a pharmaceutically acceptable solvate thereof, may be administered per se or, preferably, as a pharmaceutical composition also comprising a pharmaceutically acceptable carrier.

Accordingly, the present invention provides a pharmaceutical composition comprising a compound of formula (I) or where appropriate a pharmaceutically acceptable salt thereof and/or a pharmaceutically acceptable solvate thereof, and a pharmaceutically acceptable carrier.

The active compound may be formulated for administration by any suitable route, the preferred route depending upon the disorder for which treatment is required, and is preferably in unit dosage form or in a form that a human patient may administer to himself in a single dosage.

Advantageously, the composition is suitable for oral, rectal, topical, parenteral administration or through the respiratory tract. Preparations may be designed to give slow release of the active ingredient.

The term parenteral as used herein includes subcutaneous injections, intravenous, intramuscular, intrasternal injection or infusion tecniques. In addition to the treatment of warm-blooded animals such as mice, rats, horses, cattle, sheep, dogs, cats, etc, the compounds of the invention are effective in the treatment of humans.

The compositions of the invention may be in the form of tablets, capsules, sachets, vials, powders, granules, lozenges, suppositories, reconstitutable powders, or liquid preparations such as oral or sterile parenteral solutions or suspensions. Topical formulations are also envisaged where appropriate.

In order to obtain consistency of administration it is preferred that a composition of the invention is in the form of a unit dose. Unit dose presentation forms for oral administration may be tablets and capsules and may contain conventional excipients such as binding agents, for example syrup, acacia, gelatin, sorbitol, tragacanth, or polyvinylpyrrolidone; fillers for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers.

Such operations are of course conventional in the art. The tablets may be coated according to methods well known in normal pharmaceutical practice, in particular with an enteric coating.

Oral liquid preparations may be in the form of, for example, emulsions, syrups or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and is desired conventional flavouring or colouring agents.

Compositions may also suitably be presented for administration to the respiratory tract as a snuff or an aerosol or solution for a nebuliser, or as a microfine powder for insufflation, alone or in combination with an inert carrier such as lactose. In such a case the particles of active compound suitably have diameters of less than 50 microns, such as from 0.1 to 50 microns, preferably less than 10 microns, for example from 1 to 10 microns, 1 to 5 microns or from 2 to 5 microns. Where appropriate, small amounts of other anti-asthmatics and bronchodilators for example sympathomimetic amines such as isoprenaline, isoetharine, salbutamol, phenylephrine and ephedrine; corticosteroids such as prednisolone and adrenal stimulants such as ACTH may be included.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilised before filling into a suitable vial or ampoule and sealing.

Advantageously, adjuvants such as local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

Compounds of formula (I), or if appropriate a pharmaceutically acceptable salt thereof and/or a pharmaceutically acceptable solvate thereof, may also be administered as a topical formulation in combination with conventional topical excipients.

Topical formulations may be presented as, for instance, ointments, creams or lotions, impregnated dressings, gels, gel sticks, spray and aerosols, and may contain appropriate conventional additives such as preservatives, solvents to assist drug penetration and emollients in ointments and creams. The formulations may contain compatible conventional carriers, such as cream or ointment bases and ethanol or oleyl alcohol for lotions.

Suitable cream, lotion, gel, stick, ointment, spray or aerosol formulations that may be used for compounds of formula (I) or if appropriate a pharmaceutically acceptable salt thereof, are conventional formulations well known in the art, for example, as described in standard text books such as Harry's Cosmeticology published by Leonard Hill Books, Remington's Pharmaceutical Sciences, and the British and US Pharmacopoeias.

Suitably, the compound of formula (I), or if appropriate a pharmaceutically acceptable salt thereof, will comprise from about 0.5 to 20% by weight of the formulation, favourably from about 1 to 10%, for example 2 to 5%.

The dose of the compound used in the treatment of the invention will vary in the usual way with the seriousness of the disorders, the weight of the sufferer, and the relative efficacy of the compound. However, as a general guide suitable unit doses may be 0.1 to 1000 mg, such as 0.5 to 200, 0.5 to 100 or 0.5 to 10 mg, for example 0.5, 1, 2, 3, 4 or 5 mg; and such unit doses may be administered more than once a day, for example 2, 3, 4, 5 or 6 times a day, but preferably 1 or 2 times per day, so that the total daily dosage for a 70 kg adult is in the range of about 0.1 to 1000 mg, that is in the range of about 0.001 to 20 mg/kg/day, such as 0.007 to 3, 0.007 to 1.4, 0.007 to 0.14 or 0.01 to 0.5 mg/kg/day, for example 0.01, 0.0.02, 0.04, 0.05, 0.06, 0.08, 0.1 or 0.2 mg/kg/day, and such therapy may extend for a number of weeks or months.

When used herein the term "pharmaceutically acceptable" encompasses materials suitable for both human and veterinary use. No toxicological effects have been established for compounds of formula (I) in the above mentioned dosage ranges.

The following Examples illustrate the invention.

EXAMPLE 1

1-Ethyl-1,4-dihydro-7-methyl-N-(2-(4-pyridyl)-ethyl)-1,8-napthyridin-4-one-3-carboxamide Nalidixic acid (0.45 g) and dichloromethane (20 ml) were combined and cooled to 0° C. under nitrogen. Triethylamine (0.3 ml) was then added, followed by isopropenylchloroformate (0.24 ml) and the whole stirred for 90 minutes. 4-(2-Aminoethyl)pyridine (0.26 ml) was then added and stirring continued for 20 h, after which time the reaction was concentrated onto silica and purified by flash chromatography to give the title compound as an off white solid.

TLC $R_f$=0.29 (10% MeOH/CH$_2$Cl$_2$) m.p=170° C.

EXAMPLE 2

8-Ethyl-5,8-dihydro-5-oxo-N-(2-(2-pyridyl)ethyl)-2-(1-pyrrolidinyl)pyrido[2,3-d]pyrimidine-6-carboxamide The title compound was prepared in a similar manner to Example 1; thus 0.51 g piromidic acid and 0.23 ml 2-aminoethylpyridine gave 0.56 g of the title compound as an off white solid.

TLC $R_f$=0.54 (10% MeOH/CH$_2$Cl$_2$) IR (nujol mull)/cm$^{-1}$: 3188 (NH), 1661, 1607 (C=O)

EXAMPLE 3

8-Ethyl-5,8-dihydro-5-oxo-N-(2-(4-pyridyl)ethyl)-2-(1-pyrrolidinyl)pyrido[2,3-d]pyrimidine-6-carboxamide The title compound was prepared in a similar manner to Example 2.

TLC $R_f$=0.45 (10% MeOH/CH$_2$Cl$_2$) m.p=175°–177° C.

EXAMPLE 4

8-Ethyl-5,8-dihydro-5-oxo-N-phenylethyl-2-(1-pyrrolidinyl)pyrido[2,3-d]pyrimidine-6-carboxamide The title compound was prepared in a similar manner to Example 2.

TLC $R_f$=0.5 (5% MeOH/CH$_2$Cl$_2$) m.p=178°–180° C.

EXAMPLE 5

8-Ethyl-5,8-dihydro-5-oxo-2-(1-pyrrolidinyl)-N-(1-tetralinyl)pyrido[2,3-d]pyrimidine-6-carboxamide The title compound was prepared in a similar manner to Example 2.

TLC $R_f$=0.58 (5% MeOH/CH$_2$Cl$_2$) m.p=284°–286° C.

EXAMPLE 6

8-Ethyl-5,8-dihydro-5-oxo-2-(1-pyrrolidinyl)-N-(1-tetralinyl)pyrido[2,3-d]pyrimidine-6-carboxamide hydrochloride To a solution of Example 5 (100 mg) in CHCl$_3$ (1 ml), 1M ethereal HCl (0.24 ml) was added dropwise. The resulting solution was stirred at room temperature for 15 minutes then evaporated to dryness to give the title compound.

$^1$H NMR (200 MHz, CDCl$_3$) 1.50 (m, 3H), 1.6–2.2 (m, 8H), 2.8 (m, 2H), 3.5–4.0 (m, 4H), 4.35 (m, 2H), 5.4 (m, 1H), 7–7.5 (m, 4H), 8.8 (brs, 1H), 9.3 (brs, 1H), 10 (m, 1H) m.p=271°–273° C.

EXAMPLE 7

8-Ethyl-5,8-dihydro-N-(1-indanyl)-5-oxo-2-(1-pyrrolidinyl)pyrido[2,3-d]pyrimidine-6-carboxamide The title compound was prepared in a similar manner to Example 2.

TLC $R_f$=0.675 (10% MeOH/CH$_2$Cl$_2$) m.p=109°–210° C.

EXAMPLE 8

8-Ethyl-5,8-dihydro-N-(2-indanyl)-5-oxo-2-(1-pyrrolidinyl)pyrido[2,3-d]pyrimidine-6-carboxamide The title compound was prepared in a similar manner to Example 2.

TLC $R_f$=0.625 (10% MeOH/CH$_2$Cl$_2$) m.p=252°–253° C.

EXAMPLE 9

8-Ethyl-5,8-dihydro-N-(1-indanyl)-5-oxo-2-(1-pyrrolidinyl)pyrido[2,3-d]pyrimidine-6-carboxamide hydrochloride The title compound was prepared from Example 7 in a similar manner to Example 54.

$^1$H NMR (200 MHz, CDCl$_3$) 1.55 (m, 3H), 2–2.3 (m, 4H), 2.6–3.3 (m, 4H), 3.7–4.2 (m, 4H), 4.4 (m, 2H), 5.7 (q, 1H), 7.1–7.5 (m, 4H), 8.8 (brs, 1H), 9.35 (brs, 1H), 9.8 (brs, 1H) m.p=215°–216° C.

EXAMPLE 10

8-Ethyl-5,8-dihydro-N-(2-indanyl)-5-oxo-2-(1-pyrrolidinyl)pyrido[2,3-d]pyrimidine-6-carboxamide hydrochloride The title compound was prepared from Example 8 in a similar manner to Example 54.

$^1$H NMR (200 MHz, CDCl$_3$) 1.5 (m, 3H), 2.15 (m, 4H), 2.9–3.2 (m, 2H), 3.45 (dd, 2H), 3.6–4.0 (m, 4H), 4.4 (m, 2H), 4.95 (q, 1H), 7.1–7.4 (m, 4H), 8.7 (brs, 1H), 9.3 (brs, 1H), 10.0 (brs, 1H) m.p=256°–257° C.

EXAMPLE 11

8-Ethyl-5,8-dihydro-5-oxo-N-(2-phenylcyclopropyl)-2-(1-pyrrolidinyl)pyrido[2,3-d]pyrimidine-6-carboxamide The title compound was prepared in a similar manner to Example 2.

TLC $R_f$=0.5 (5% MeOH/CH$_2$Cl$_2$) m.p=199°–201° C.

EXAMPLE 12

N-Cyclohexyl-8-Ethyl-5,8-dihydro-5-oxo-2-(1-pyrrolidinyl)pyrido[2,3-d]pyrimidine-6-carboxamide The title compound was prepared in a similar manner to Example 2.

TLC $R_f$=0.3 (5% MeOH/CH$_2$Cl$_2$) m.p=265°–267° C.

EXAMPLE 13

N-Cyclohexyl-8-Ethyl-5,8-dihydro-5-oxo-2-(1-pyrrolidinyl)pyrido[2,3-d]pyrimidine-6-carboxamide hydrochloride The title compound was prepared from Example 12 in a similar manner to Example 6.

EXAMPLE 14

8-Ethyl-5,8-dihydro-5-oxo-N-(2-phenylcyclopropyl)-2-(1-pyrrolidinyl)pyrido[2,3-d]pyrimidine-6-carboxamide hydrochloride The title compound was prepared from Example 11 in a similar manner to Example 6.

$^1$H NMR (200 MHz, DMSO) 1.2–1.4 (m, 5H), 1.9–2.2 (m, 5H), 3.0 (m, 1H), 3.6 (m, 4H), 4.4 (q, 1H), 7.1–7.4 (m, 5H), 8.75 (s, 1H), 9.1 (s, 1H), 10.0 (d, 1H)

m.p=196°–199° C.

EXAMPLE 15

8-Ethyl-5,8-dihydro-5-oxo-2-(1-pyrrolidinyl)-N-(2-tetralinyl)pyrido[2,3-d]pyrimidine-6-carboxamide hydrochloride The title compound was prepared in a similar manner to Example 6.

$^1$H NMR (200 MHz, DMSO) 1.35 (t, 3H), 1.9–2.1 (m, 5H), 2.6–3.2 (m, 4H), 3.5–3.7 (m, 4H), 4.2–4.5 (m, 3H), 7–7.2 (m, 4H), 8.75 (s, 1H), 9.1 (s, 1H), 9.95 (d, 1H) m.p=264°–65° C.

EXAMPLE 16

N-(1-(5,6-Dimethoxy)indanyl)-8-ethyl-5,8-dihydro-5-oxo-2-(1-pyrrolidinyl)pyrido[2,3-d]pyrimidine-6-carboxamide The title compound was prepared in a similar manner to Example 2.

TLC $R_f$=0.175 (5% MeOH/CH$_2$Cl$_2$) m.p=204°–205° C.

EXAMPLE 17

N-(1-(5,6-Dimethoxy)indanyl)-8-ethyl-5,8-dihydro-5-oxo-2-(1-pyrrolidinyl)pyrido[2,3-d]pyrimidine-6-carboxamide hydrochloride The title compound was prepared from Example 16 in a similar manner to Example 6.

$^1$H NMR (200 MHz, CDCl$_3$) 1.4–1.6 (m, 3H), 2.0–2.3 (m, 4H), 2.5–3.3 (m, 4H), 3.6–4.1 (m, 4H), 3.9 (s, 3H), 3.95 (s, 3H), 4.4 (m, 2H), 5.7 (m, 1H), 6.8 (s, 1H), 6.9 (s, 1H), 8.8 (brs, 1H), 9.3 (brs, 1H), 10 (brs, 1H) m.p=115°–116° C.

EXAMPLE 18

N-(1-(5-Acetamido)indanyl)-8-ethyl-5,8-dihydro-5-oxo-2-(1-pyrrolidinyl)pyrido[2,3-d]pyrimidine-6-carboxamide The title compound was prepared in a similar manner to Example 2.

TLC $R_f$=0.5 (5% MeOH/CH$_2$Cl$_2$) m.p=305°–307° C.

EXAMPLE 19

N-(1-(6-Acetamido)tetralinyl)-8-ethyl-5,8-dihydro-5-oxo-2-(1-pyrrolidinyl)pyrido[2,3-d]pyrimidine-6-carboxamide The title compound was prepared in a similar manner to Example 2.

TLC $R_f$=0.11 (5% MeOH/CH$_2$Cl$_2$) m.p=182°–185° C.

EXAMPLE 20

N-(1-(6-Acetamido)tetralinyl)-8-ethyl-5,8-dihydro-5-oxo-2-(1-pyrrolidinyl)pyrido[2,3-d]pyrimidine-6-carboxamide hydrochloride The title compound was prepared from Example 19 in a similar manner to Example 6.

$^1$H NMR (200 MHz, CDCl$_3$) 1.4–1.7 (m, 3H), 1.7–2.5 (m, 11H), 2.6–3.0 (m, 2H), 3.7–4.6 (m, 6H), 5.35 (m, 1H), 7.1–7.5 (m, 4H), 8.4 (brs, 1H), 9.3 (brs, 1H), 9.7 (brs, 1H) m.p=135°–140° C.

EXAMPLE 21

8-Ethyl-5,8-dihydro-5-oxo-N-(2-(4-pyridyl)ethyl)-2-(1-pyrrolidinyl)pyrido[2,3-d]pyrimidine-6-carboxamide dihydrochloride The title compound was prepared from Example 3 in a similar manner to Example 6.

$^1$H NMR (200 MHz, DMSO) 1.35 (t, 3H), 1.95 (m, 4H), 3.15 (t, 2H), 3.5–3.8 (m, 6H), 4.35 (q, 2H), 8.0 (d, 2H), 8.7 (s, 1H), 8.85 (d, 2H), 9.1 (s, 1H), 9.8 (t, 1H) m.p=279°–280° C.

EXAMPLE 22

N-[1-(5-Chloro)indanyl]-8-ethyl-5,8-dihydro-5-oxo-2-(1-pyrrolidinyl)pyrido[2,3-d]pyrimidine-6-carboxamide The title compound was prepared in a similar manner to Example 2.

TLC $R_f$=0.53 (10% MeOH/CH$_2$Cl$_2$) $^1$H NMR (200 MHz, CDCl$_3$) 1.5 (t, 3H), 2.0–2.3 (m, 5H), 2.6–3.2 (m, 3H), 3.6–3.85 (m, 4H), 4.4 (q, 2H), 5.65 (q, 1H), 7.1–7.4 (m, 3H), 8.75 (s, 1H), 9.3 (s, 1H), 10.2 (d, 1H)

EXAMPLE 23

N-[1-(5-Chloro)indanyl]-8-ethyl-5,8-dihydro-5-oxo-2-(1-pyrrolidinyl)pyrido[2,3-d]pyrimidine-6-carboxamide hydrochloride The title compound was prepared from Example 22 in a similar manner to Example 6.

$^1$H NMR (200 MHz, CDCl$_3$) 1.5 (t, 3H), 2.0–2.3 (m, 5H), 2.6–3.2 (m, 3H), 3.6–3.85 (m, 4H), 4.4 (q, 2H), 5.65 (q, 1H), 7.1–7.4 (m, 3H), 8.75 (s, 1H), 9.3 (s, 1H), 10.2 (d, 1H) m.p=235°–238° C.

EXAMPLE 24

N-[1-(6-Acetamido)indanyl]-8-ethyl-5,8-dihydro-5-oxo-2-(1-pyrrolidinyl)pyrido[2,3-d]pyrimidine-6-carboxamide The title compound was prepared in a similar manner to Example 2.

TLC $R_f$=0.5 (10% MeOH/CH$_2$Cl$_2$) m.p=212°–214° C.

EXAMPLE 25

8-Ethyl-5,8-dihydro-N-[1-(3-methoxycarbonyl)indanyl]-5-oxo-2-(1-pyrrolidinyl)pyrido[2,3-d]pyrimidine-6-carboxamide The title compound was prepared in a similar manner to Example 2.

TLC $R_f$=0.28 (5% MeOH/CH$_2$Cl$_2$) $^1$H NMR (200 MHz, CDCl$_3$) 1.5 (t, 3H), 2.1 (m, 4H), 2.2–2.5 (m, 1H), 2.9–3.2 (m, 1H), 3.6–3.8 (m,4H), 3.75 (s, 3H), 4.1 (t, 0.5H), 4.25–4.5 (m, 2.5H), 5.8 (q, 0.5H), 5.95 (q, 0.5H), 7.3–7.55 (m, 4H), 8.75 (s, 1H), 9.3 (s, 0.5H), 9.35 (s, 0.5H), 10.2 (d, 0.5H), 10.4 (d, 0.5H)

EXAMPLE 26

8-Ethyl-5,8-dihydro-N-[1-(3-methoxycarbonyl)indanyl]-5-oxo-2-(1-pyrrolidinyl)pyrido[2,3-d]pyrimidine-6-carboxamide hydrochloride The title compound was prepared from Example 25 in a similar manner to Example 6.

$^1$H NMR (200 MHz, CDCl$_3$) 1.5 (t, 3H), 2.1 (m, 4H), 2.2–2.5 (m, 1H), 2.9–3.2 (m, 1H), 3.6–3.8 (m, 4H), 3.75 (s, 3H), 4.1 (t, 0.5H), 4.25–4.5 (m, 2.5H), 5.8 (m, 0.5H), 5.95 (m, 0.5H), 7.3–7.55 (m, 4H), 8.75 (s, 1H), 9.3 (s, 0.5H), 9.35 (s, 0.5H), 10.2 (m, 0.5H), 10.4 (m, 0.5H) m.p=226°–228° C.

EXAMPLE 27

8-Ethyl-5,8-dihydro-N-[1-(3-carboxy)indanyl]-5-oxo-2-(1-pyrrolidinyl)pyrido[2,3-d]pyrimidine-6-carboxamide Example 25 (100 mg), tetrahydrofuran (15 ml), water (15 ml) and lithium hydroxide monohydrate (18.5 mg) were combined and the whole stirred for 16 h. The tetrahydrofuran was then removed in vacuo and the aqueous acidified with conc. HCl with ice bath cooling. The resulting precipitate was collected by filtration and dried to give the title compound as a yellow solid.

$^1$H NMR (200 MHz, DMSO) 1.3 (t, 3H), 1.8–2.2 (m, 5H), 2.65–2.9 (m, 1H), 3.4–3.7 (m, 4H), 3.9 (m, 3H), 5.4–5.7 (m, 1H), 7.2–7.5 (m, 4H), 8.8 (s, 1H), 9.05 (s, 1H), 10.05–10.3 (m, 1H) m.p=256°–259° C.

ASSAY METHODS

The assays used to confirm the phosphodiesterase IV inhibitory activity of compounds of formula (I) are standard assay procedures as disclosed by Schilling et al An. Biochem. 216154 (1994), Thompson and Strada, Adv. Cycl. Nucl. Res. 8:119 (1979) and Gristwood and Owen, Br. J. Pharmacol. 87:91P (1985). Compounds of formula (I) have exhibited activity at levels consistent with those believed to be useful in treating phosphodiesterase IV related disease states in those assays.

The potency of the compounds of formula (I) as inhibitors of the production of TNF was determined using the following procedure. A 1 mM solution of the inhibitor being tested, or dilutions thereof, was incubated at 37° C. in an atmosphere of 5% CO$_2$ with THP.1 cells at a density of 1×10$^6$/ml and stimulated with 5 mg/ml final concentration of LPS, i.e. lipopolysaccharide (endotoxin). After 18 hours the supernatant was assayed for the levels of TNF using commercially available enzyme linked immunosorbent assay (ELISA) kits (R and D Systems).

We claim:

1. A method for treating a mammal having a disease state capable of being modulated by inhibition of the activity or production of phosphodiesterase IV or tumour necrosis factor, wherein said method comprises administering to said mammal an effective amount of a compound of formula (I)

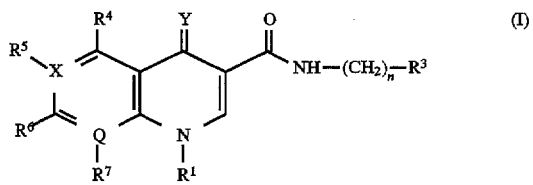

in which:

$R^1$ is $C_{1-6}$ alkyl, $C_{1-6}$ alkylcycloalkyl, $C_{1-6}$ alkylheterocyclic, $C_{1-6}$ alkylaryl or $C_{1-6}$ alkylheteroaryl, any of which is optionally substituted by one or more substituents selected from the group consisting of halo, $C_{1-6}$ alkoxy, hydroxy, CN, CO$_2$H (or $C_{1-6}$ alkyl esters or $C_{1-6}$ alkyl amides thereof), $C_{1-6}$ alkyl, NR$^9$R$^{10}$ and SO$_2$NR$^{11}$R$^{12}$;

$R^3$ pyridyl, thienyl, furyl, pyrazinyl, pyridazinyl, pyrimidinyl, or $C_{3-10}$ cycloalkyl, to any of which is optionally fused a second, carboxylic or heterocyclic ring, and wherein the, or each, ring is optionally substituted at any available position by one or more substituents selected from the group consisting of halogens, $C_{1-6}$ alkoxy, OH, CN, $C_{1-6}$ alkyl amide, $C_{1-6}$ alkyl, $C_{1-6}$ haloalkyl, NR$^9$R$^{10}$, SO$_2$NR$^{11}$R$^{12}$, aryl, heteroaryl, cycloalkyl and heterocyclo;

Y is O or S;

X is N (in which case R$^5$ is absent);

Q is N (in which case R$^7$ is absent);

R$^4$, R$^5$, R$^6$ and R$^7$ are the same or different and are each H, halo, $C_{1-6}$ alkoxy, hydroxy, CN, CO$_2$H (or $C_{1-6}$ alkyl esters thereof or $C_{1-6}$ alkyl amides thereof), NR$^9$R$^{10}$ or $C_{1-6}$ alkyl, in which alkyl may be optionally substituted by halo, $C_{1-6}$ alkoxy, hydroxy, CN, CO$_2$H (or $C_{1-6}$ alkyl esters thereof or $C_{1-6}$ alkyl amides thereof), NR$^9$R$^{10}$ or SO$_2$NR$^{11}$R$^{12}$, or any two adjacent groups R$^4$–R$^7$ and the C atoms to which they are attached form a 5 or 6-membered ring containing 0, 1 or 2 heteroatoms;

either R$^9$ and R$^{10}$ are the same or different and are each H, $C_{1-6}$ alkyl, aryl, heteroaryl, COCF$_3$, SO$_2$CF$_3$, cycloalkyl, $C_{1-6}$ alkylcarbonyl, arylcarbonyl, $C_{1-6}$ alkoxycarbonyl, arylsulphonyl or $C_{1-6}$ alkylsulphonyl; or NR$^9$R$^{10}$ is a 5 or 6-membered ring such as pyrrolidine, piperidine, morpholine, or piperazine ring;

R$^{11}$ and R$^{12}$ are the same or different and are each H, $C_{1-6}$ alkyl or cycloalkyl; and n=0–3;

or a pharmaceutically-acceptable salt, solvate, hydrate or combination thereof.

2. The method of claim 1, wherein R$^1$ is not alkylcycloalkyl.

3. The method of claim 2, wherein Y is O.

4. The method of claim 3, wherein $R^3$ is thienyl, furyl or cycloalkyl, no two of $R^4$–$R^7$ form a ring, and neither $R^9$ nor $R^{10}$ is aryl, heteroaryl, $COCF_3$ or $SO_2CF_3$.

5. The method of claim 3, wherein $R^3$ is pyridyl, no two of $R^4$–$R^7$ form a ring, and neither $R^9$ nor $R^{10}$ is aryl, heteroaryl, $COCF_3$ or $SO_2CF_3$.

6. The method of claim 1, wherein n=0–2.

7. The method of claim 1, wherein $R^3$ is pyridyl, pyrindanyl, indanyl or tetralinyl.

8. The method of claim 1, wherein $R^1$ is alkyl.

9. The method of claim 1, wherein the compound is selected from the group consisting of 1-Ethyl-1,4-dihydro-7-methyl-N-(2-(4-pyridyl)ethyl)-1,8-napthyridin-4-one-3-carboxamide 8-Ethyl-5,8-dihydro-5-oxo-N-(2-(2-pyridyl)ethyl)-2-(1-pyrrolidinyl)pyrido[2,3-d]pyrimidine-6-carboxamide.

10. The method of claim 1, wherein the compound is selected from the group consisting from 8-Ethyl-5,8-dihydro-5-oxo-N-(2-phenylcyclopropyl)-2-(1-pyrrolidinyl)pyrido[2,3-d]pyrimidine-6-carboxamide N-Cyclohexyl-8-Ethyl-5,8-dihydro-5-oxo-2-(1-pyrrolidinyl)pyrido[2,3-d]pyrimidine-6-carboxamide N-Cyclohexyl-8-Ethyl-5,8-dihydro-5-oxo-2-(1-pyrrolidinyl)pyrido[2,3-d]pyrimidine-6-carboxamide hydrochloride 8-Ethyl-5,8-dihydro-5-oxo-N-(2-phenylcyclopropyl)-2-(1-pyrrolidinyl)pyrido[2,3-d]pyrimidine-6-carboxamide hydrochloride 8-Ethyl-5,8-dihydro-5-oxo-2-(1-pyrrolidinyl)-N-(2-tetralinyl)pyrido[2,3-d]pyrimidine-6-carboxamide hydrochloride N-(1-(5,6-Dimethoxy)indanyl)-8-ethyl-5,8-dihydro-5-oxo-2-(1-pyrrolidinyl)pyrido[2,3-d]pyrimidine-6-carboxamide N-(1-(5,6-Dimethoxy)indanyl)-8-ethyl-5,8-dihydro-5-oxo-2-(1-pyrrolidinyl)pyrido[2,3-d]pyrimidine-6-carboxamide hydrochloride N-(1-(5-Acetamido)indanyl)-8-ethyl-5,8-dihydro-5-oxo-2-(1-pyrrolidinyl)pyrido[2,3-d]pyrimidine-6-carboxamide N-(1-(6-Acetamido)tetralinyl)-8-ethyl-5,8-dihydro-5-oxo-2-(1-pyrrolidinyl)pyrido[2,3-d]pyrimidine-6-carboxamide N-(1-(6-Acetamido)tetralinyl)-8-ethyl-5,8-dihydro-5-oxo-2-(1-pyrrolidinyl)pyrido[2,3-d]pyrimidine-6-carboxamide hydrochloride 8-Ethyl-5,8-dihydro-5-oxo-N-(2-(4-pyridyl)ethyl)-2-(1-pyrrolidinyl)pyrido[2,3-d]pyrimidine-6-carboxamide dihydrochloride.

11. The method of claim 1, wherein the compound is selected from

N-[1-(5-Chloro)indanyl]-8-ethyl-5,8-dihydro-5-oxo-2-(1-pyrrolidinyl)pyrido[2,3-d]pyrimidine-6-carboxamide N-[1-(5-Chloro)indanyl]-8-ethyl-5,8-dihydro-5-oxo-2-(1-pyrrolidinyl)pyrido[2,3-d]pyrimidine-6-carboxamide hydrochloride N-[1-(6-Acetamido)indanyl]-8-ethyl-5,8-dihydro-5-oxo-2-(1-pyrrolidinyl)pyrido[2,3-d]pyrimidine-6-carboxamide 8-Ethyl-5,8-dihydro-N-[1-(3-methoxycarbonyl)indanyl]-5-oxo-2-(1-pyrrolidinyl)pyrido[2, 3-d]pyrimidine-6-carboxamide 8-Ethyl-5,8-dihydro-N-[1-(3-methoxycarbonyl)indanyl]-5-oxo-2-(1-pyrrolidinyl)pyrido[2,3-d]pyrimidine-6-carboxamide hydrochloride 8-Ethyl-5,8-dihydro-N-[1-(3-carboxy)indanyl]-5-oxo-2-(1-pyrrolidinyl)pyrido[2,3-d]pyrimidine-6-carboxamide.

12. The method of claim 1, wherein the compound is in the form of an enantiomer, or mixture of enantiomers.

13. The compound as defined in claim 12, with the proviso that when $R^3$ is attached to $(CH_2)_n$ at an aromatic atom, n=1–3.

14. The compound of claim 13, wherein Y is O and either $R^3$ is thienyl, furyl or cycloalkyl, no two of $R^4$–$R^7$ form a ring, and neither $R^9$ nor $R^{10}$ is aryl, heteroaryl, $COCF_3$, or $SO_2CF_3$; or $R^3$ is pyridyl, no two of $R^4$–$R^7$ form a ring, and neither $R^9$ nor $R^{10}$ is aryl, heteroaryl, $COCF_3$ or $SO_2CF_3$.

15. The method of claim 1, with the proviso that when $R^3$ is attached to $(CH_2)_n$ at an aromatic atom, n=1–3.

16. The method of claim 1, wherein the disease state is a pathological condition associated with a function of phosphodiesterase IV, eosinophil accumulation or a function of the eosinophil.

17. The method of claim 16, wherein the pathological condition is selected from asthma, chronic bronchitis, atopic dermatitis, urticaria, allergic rhinitis, allergic conjunctivitis, vernal conjunctivitis, inflammation of the eye, allergic responses in the eye, eosinophilic granuloma, psoriasis, rheumatoid arthritis, gouty arthritis and other arthritic conditions, ulcerative colitis, Crohn's disease, adult respiratory distress syndrome, diabetes insipidus, keratosis, atopic eczema, atopic dermatitis, cerebral senility, multiinfarct dementia, senile dementia, memory impairment associated with Parkinson's disease, depression, cardiac arrest, stroke and intermittent claudication.

18. The method of claim 17, wherein the pathological condition is selected from chronic bronchitis, allergic rhinitis and adult respiratory distress syndrome.

19. The method of claim 1, wherein the disease state is capable of being modulated by TNF inhibition.

20. The method of claim 19, wherein the disease state is an inflammatory disease or autoimmune disease.

21. The method of claim 20, wherein the disease state is selected from the group consisting of joint inflammation, arthritis, rheumatoid arthritis, rheumatoid spondylitis and osteoarthritis, sepsis, septic shock, endotoxic shock, gram negative sepsis, toxic shock syndrome, acute respiratory distress syndrome, cerebral malaria, chronic pulmonary inflammatory disease, pulmonary sarcoidosis, asthma, bone resorption diseases, reperfusion injury, graft vs host reaction, allograft rejection, malaria, myalgias, HIV, AIDS, ARC, cachexia, Crohn's disease, ulcerative colitis, pyresis, systemic lupus erythematosus, multiple sclerosis, type 1 diabetes mellitus, psoriasis, Bechet's disease, anaphylactoid purpura nephritis, chronic glomerulonephritis, inflammatory bowel disease and leukaemia.

22. The method of claim 17, wherein the pathological condition is asthma.

23. The method of claim 21, wherein the disease state is selected from the group consisting of acute respiratory distress syndrome, pulmonary inflammatory disease and pulmonary sarcoidosis.

24. The method of claim 21, wherein the disease state is joint inflammation.

25. The method of claim 16, wherein the disease state is tardive dyskinesia.

26. The method of claim 19, wherein the disease state is a yeast or fungal infection.

27. The method of claim 1, for gastroprotection.

28. The method of claim 1, wherein Y is O and either $R^3$ is phenyl, thienyl, furyl or cycloalkyl, no two of $R^4$–$R^7$ form a ring, and neither $R^9$ nor $R^{10}$ is aryl, heteroaryl, $COCF_3$, or $SO_2CF_3$; or $R^3$ is pyridyl, no two of $R^4$–$R^7$ form a ring, and neither $R^9$ nor $R^{10}$ is aryl, heteroaryl, $COCF_3$ or $SO_2CF_3$.

29. The method of claim 21, wherein the disease state is asthma.

30. The method of claim 20, wherein the disease state is tardive dyskinesia.

31. A compound of formula (I)

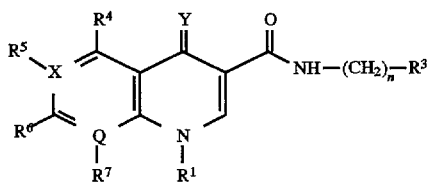

in which:

$R^1$ is $C_{1-6}$ alkyl, $C_{1-6}$ alkylcycloalkyl, $C_{1-6}$ alkylheterocyclic, $C_{1-6}$ alkylaryl or $C_{1-6}$ alkyheteroaryl, any of which is optionally substituted by one or more substituents selected from the group consisting of halo, $C_{1-6}$ alkoxy, hydroxy, CN, $CO_2H$ (or $C_{1-6}$ alkyl esters or $C_{1-6}$ alkyl amides thereof), $C_{1-6}$ alkyl, $NR^9R^{10}$ and $SO_2NR^{11}R^{12}$;

$R^3$ is pyridyl, thienyl, furyl, pyrazinyl, pyridazinyl, pyrimidinyl, or $C_{3-10}$ cycloalkyl, to any of which is optionally fused a second, carboxylic or heterocyclic ring, and wherein the, or each, ring is optionally substituted at any available position by one or more substituents selected from the group consisting of halogens, $C_{1-6}$ alkoxy, OH, CN, $C_{1-6}$ alkyl amide, $C_{1-6}$ alkyl, $C_{1-6}$ haloalkyl, $NR^9R^{10}$, $SO_2NR^{11}R^{12}$, aryl, heteroaryl, cycloalkyl and heterocyclo;

Y is O or S;

X is N (wherein $R^5$ is absent);

Q is N (wherein $R^7$ is absent);

$R^4$, $R^5$, $R^6$ and $R^7$ are the same or different and are each H, halo, $C_{1-6}$ alkoxy, hydroxy, CN, $CO_2H$ (or $C_{1-6}$ alkyl esters thereof or $C_{1-6}$ alkyl amides thereof), $NR^9R^{10}$ or $C_{1-6}$ alkyl, in which alkyl may be optionally substituted by halo, $C_{1-6}$ alkoxy, hydroxy, CN, $CO_2H$ (or $C_{1-6}$ alkyl esters thereof or $C_{1-6}$ alkyl amides thereof), $NR^9R^{10}$ or $SO_2NR^{11}R^{12}$, or any two adjacent groups $R^4$–$R^7$ and the C atoms to which they are attached form a 5 or 6-membered ring containing 0, 1 or 2 heteroatoms;

either $R^9$ and $R^{10}$ are the same or different and are each H, $C_{1-6}$ alkyl, aryl, heteroaryl, $COCF_3$, $SO_2CF_3$, cycloalkyl, $C_{1-6}$ alkylcarbonyl, arylcarbonyl, $C_{1-6}$ alkoxycarbonyl, arylsulphonyl or $C_{1-6}$ alkylsulphonyl; or $NR^9R^{10}$ is a 5 or 6-membered ring such as pyrrolidine, piperidine, morpholine, or piperazine ring;

$R^{11}$ and $R^{12}$ are the same or different and are each H, $C_{1-6}$ alkyl or cycloalkyl; and n=0–3;

or a pharmaceutically-acceptable salt, solvate, hydrate or combination thereof.

* * * * *